United States Patent [19]
Yamada et al.

[11] Patent Number: 5,847,122
[45] Date of Patent: Dec. 8, 1998

[54] PROCESS FOR PREPARING 1,5-BENZOTHIAZEPINE DERIVATIVE

[75] Inventors: Shinichi Yamada, Takarazuka; Ryuzo Yoshioka, Mishima-gun; Takeji Shibatani, Kobe, all of Japan

[73] Assignee: Tanabe Seiyaku Co., Ltd., Osaka, Japan

[21] Appl. No.: 804,000

[22] Filed: Feb. 21, 1997

[30] Foreign Application Priority Data

Feb. 23, 1996 [JP] Japan .................................. 8-035302

[51] Int. Cl.⁶ .................................................. C07D 281/02
[52] U.S. Cl. ............................................................ 540/491
[58] Field of Search ............................................. 540/491

[56] References Cited

U.S. PATENT DOCUMENTS

| | | | |
|---|---|---|---|
| 3,562,257 | 2/1971 | Kugita et al. | 260/239.3 |
| 4,438,035 | 3/1984 | Gaino et al. | 260/239.3 |
| 4,567,175 | 1/1986 | Takeda et al. | 514/211 |
| 4,959,359 | 9/1990 | Mohacsi et al. | 540/488 |
| 5,102,998 | 4/1992 | Rossey et al. | 540/491 |
| 5,134,139 | 7/1992 | Kawai et al. | 540/491 |
| 5,294,706 | 3/1994 | Koumoto et al. | 540/491 |
| 5,378,698 | 1/1995 | Yamamori et al. | 540/491 |

FOREIGN PATENT DOCUMENTS

| | | |
|---|---|---|
| 0343474 | 11/1989 | European Pat. Off. . |
| 0450705 | 10/1991 | European Pat. Off. . |
| 46-43785 | 12/1971 | Japan . |
| 53-18038 | 6/1978 | Japan . |
| 5202013 | 8/1993 | Japan . |
| WO9507359 | 3/1995 | WIPO . |

OTHER PUBLICATIONS

Organic Chemistry, 3(13–1):501–516 (1970).
Miyata et al., Tetrahedron Letters 32(29):3519–3522 (1991).
Kugita et al., Chem. Pharm. Bull. 18(10):2028–2037 (1970).
Baldas et al., Australian Journal of Chemistry, vol. 20, No. 12, pp. 2655–2668 (1967).
Miyata et al., Tetrahedron Letters, 32(29):3519–3522 (1991).

*Primary Examiner*—John M. Ford
*Attorney, Agent, or Firm*—Birch, Stewart, Kolasch & Birch, LLP

[57] ABSTRACT

A novel process for preparing 1,5-benzothiazepine derivative [II]:

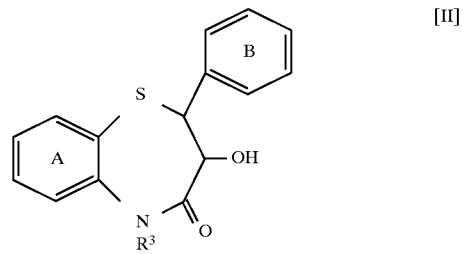

wherein Ring A and Ring B are substituted or unsubstituted benzene ring, and $R^3$ is H, (di-lower alkylamino)-lower alkyl or substituted or unsubstituted piperazinyl-lower alkyl, or a salt thereof, in high yield and in a single step from a novel 3-(2-amino-substituted or unsubstituted phenylthio)-2-hydroxy-3-substituted or unsubstituted phenylpropionamide compound. Said 1,5-benzothiazepine derivative [II] is useful as an intermediate for preparing medicaments such as diltiazem hydrochloride.

22 Claims, No Drawings

PROCESS FOR PREPARING 1,5-BENZOTHIAZEPINE DERIVATIVE

TECHNICAL FIELD

The present invention relates to a novel process for preparing a 1,5-benzothiazepine derivative which is useful as an intermediate for preparing medicaments.

PRIOR ART

Diltiazem hydrochloride (chemical name; (2S,3S)-3-acetoxy-5-[2-(dimethylamino)ethyl]-2,3-dihydro-2-(4-methoxyphenyl)-1,5-benzothiazepin-4(5H)-one hydrochloride) has been widely used as a calcium channel blocker in the treatment of angina pectoris, essential hypertension, etc., and it is usually prepared by dimethylaminoethylating the 5-position and acetylating the 3-hydroxy group of cis-3-hydroxy-2,3-dihydro-2-(4-methoxyphenyl)-1,5-benzothiazepin-4(5H)-one (cf. U.S. Pat. Nos. 3,562,257 and 4,438,035).

Hitherto, as a process for preparing cis-3-hydroxy-2,3-dihydro-2-(4-methoxyphenyl)-1,5-benzothiazepin-4(5H)-one, an intermediate for diltiazem hydrochloride, there is known a process which comprises reacting 3-(4-methoxyphenyl)-2,3-epoxypropionic acid methyl ester with 2-aminothiophenol, hydrolyzing the resulting 3-(2-aminophenylthio)-2-hydroxy-3-(4-methoxyphenyl) propionic acid methyl ester and subjecting the product to intramolecular cyclization reaction [cf. Chemical and Pharmaceutical Bulletin, p 2028, 1970].

Alternatively, the following processes have been known as a process for preparing cis-3-hydroxy-2,3-dihydro-2-(4-methoxyphenyl)-1,5-benzothiazepin-4(5H)-one by the use of a sulfonic acid without the hydrolyzing 3-(2-aminophenylthio)- 2-hydroxy-3-(4-methoxyphenyl) propionic acid ester.

(1) A process comprising reacting 2-aminothiophenol with (-)-(2R,3S)-2,3-epoxy-3-(4-methoxyphenyl)propionic acid methyl ester, and subjecting the resulting (2S,3S)-3-(2-aminophenylthio)-2-hydroxy-3-(4-methoxyphenyl) propionic acid methyl ester to intramolecular cyclization reaction in the presence of methanesulfonic acid, etc., in a chlorinated organic solvent having a boiling point of more than 70° C. (cf. U.S. Pat. No. 5,102,998).

(2) A process comprising subjecting 3-(2-aminophenylthio)-2-hydroxy-3-(4-methoxyphenyl) propionic acid methyl ester to intramolecular cyclization reaction in the presence of methanesulfonic acid, etc., in a non-halogenated organic solvent (cf. U.S. Pat. No. 5,294,706).

(3) A process comprising subjecting (2S,3S)-3-(2-aminophenylthio)-2-hydroxy-3-(4-methoxyphenyl) propionic acid (1R,2S)-2-phenylcyclohexyl ester to intramolecular cyclization reaction in the presence of p-toluenesulfonic acid monohydrate [cf. Japanese Patent First Publication (Kokai) No. 17170/1990].

The following processes have been known as a process for preparing 5-[2-(dimethylamino)ethyl]-2,3-dihydro-3-hydroxy-2-(4-methoxyphenyl)-1,5-benzothiazepin-4(5H)-one, another intermediate for diltiazem hydrochloride, by intramolecular cyclization reaction using a base.

(1) A process comprising subjecting 3-(2-aminophenylthio)-2-hydroxy-3-(4-methoxyphenyl) propionic acid methyl ester to intramolecular cyclization reaction by reacting it with N,N-dimethylaminoethyl chloride or an acid addition salt thereof in the presence of a solid alkali metal hydroxide in an ether solvent [cf. Japanese Patent First Publication (Kokai) No. 202013/1993].

(2) A process comprising subjecting 3-(2-aminophenylthio)-2-hydroxy-3-(4-methoxyphenyl) propionic acid methyl ester to intramolecular cyclization reaction in the presence of an alkali metal alkoxide in an aprotic polar solvent, and further introducing 2-(dimethylamino)ethyl group on the 5-position of the product [cf. Japanese Patent First Publication (Kokai) No. 221376/1992].

However, it is well-known among organic chemists that an amide is less easily attacked by a nucleophile than an ester is [cf. Hendrickson, Cram, Hammond, Organic Chemistry, the 3rd edition, Chapter 13-1, pp 501–516, etc.], and for forming 1,5-benzothiazepine nucleus there has been only reported an intramolecular cyclization reaction of (-)-4-isopropyl-3-[3-(2-aminophenylthio)-2-methoxyethoxymethoxy-3-(4-methoxyphenyl)propionyl]-2-oxazolidinone having activated N-acylamide group by treating it with trimethylaluminum in methylene chloride [cf. Tetrahedron Letters, 32, pp 3516–3522 (1991)].

In addition, U.S. Pat. No. 4,959,359 discloses that trans-3-(4-methoxyphenyl)-2,3-epoxypropionamide is prepared by treating trans-3-(4-methoxyphenyl)-2,3-epoxypropionic acid ester with ammonium hydroxide, and WO 95/7359 discloses that trans-3-(4-methoxyphenyl)-2,3-epoxypropionic acid methyl ester is treated with ammonia in the presence of Lipase SP 523, by which only (2S,3R)-isomer thereof is stereoselectively amidated.

BRIEF DESCRIPTION OF INVENTION

An object of the present invention is to provide an improved process for preparing a 1,5-benzothiazepine nucleus in high yield and in a single step from a novel 3-[2-amino-(substituted or unsubstituted phenylthio)]-2-hydroxy- 3-(substituted or unsubstituted phenyl) propionamide compound.

DETAILED DESCRIPTION OF INVENTION

According to the present invention, a 1,5-benzothiazepine derivative of the formula [II]:

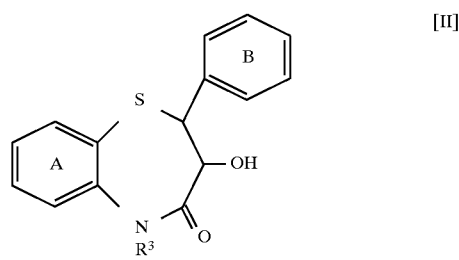

wherein Ring A and Ring B are a substituted or unsubstituted benzene ring, and $R^3$ is a hydrogen atom, a (di-lower alkylamino)-lower alkyl group or a substituted or unsubstituted piperazinyl-lower alkyl group is prepared by subjecting a propionamide derivative of the formula [I]:

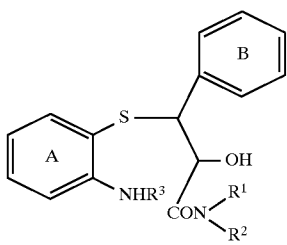

wherein $R^1$ and $R^2$ are the same or different and each are a hydrogen atom, a carbamoyl group, a lower alkyl group, a lower alkanoyl group, a lower alkylaminocarbonyl group, an amino acid residue, or an aryl group having optionally a substituent, or combine each other at their termini together with the adjacent nitrogen atom to which they bond to form a heterocyclic group having optionally a substituent, and Ring A, Ring B and $R^3$ are the same as defined above, or a salt thereof, to intramolecular cyclization reaction.

Ring A and/or Ring B in the propionamide derivative of the formula [I] may be either an unsubstituted benzene ring or benzene rings having a substituent selected from a lower alkyl group, a lower alkoxy group and a halogen atom and a phenyl-lower alkyl group at any position thereof.

Suitable examples of the Ring A are groups of the formula:

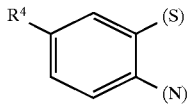

wherein $R^4$ is a hydrogen atom, a halogen atom, a lower alkyl group or a phenyl-lower alkyl group and suitable examples of the Ring B are a 4-lower alkylphenyl group and a 4-lower alkoxyphenyl group.

Among these examples of Ring A and Ring B, preferable combinations of Ring A and Ring B are (a) Ring A is a partial structure of the formula [VI] ($R^4$ is a hydrogen atom, a halogen atom or a phenyl-lower alkyl group), and Ring B is a 4-lower alkoxyphenyl group, and (b) Ring A is a partial structure of the formula [VI] ($R^4$ is a lower alkyl group), and Ring B is a 4-lower alkylphenyl group.

The amino acid residue for $R^1$ and $R^2$ includes a residue which is produced by removing one amino group from an amino acid, wherein hydroxy groups, mercapto groups, amino groups and/or carboxyl groups may optionally be protected by a protecting group. The amino acid includes either natural amino acids or synthetic amino acids, and should have at least one amino group and one carboxyl group in the molecule thereof, for example, natural amino acids or antipodes thereof, synthetic D- or L-amino acids or racemic mixtures thereof. Preferable amino acids are α-amino acids and β-amino acids.

These amino acids may be either neutral amino acids, acidic amino acids or basic amino acids, and the neutral amino acids are amino acids having amino groups and carboxyl groups in the same numbers such as alanine, isoleucine, leucine, etc., amino acids having a hydroxy group such as serine, threonine, tyrosine, etc., sulfur-containing amino acids such as cysteine, cystine, methionine, etc. The acidic amino acids are amino acids having more carboxyl groups than amino groups such as glutamic acid, aspartic acid, etc., and the basic amino acids are amino acids having more amino groups than carboxyl groups such as arginine, ornithine, lysine, etc. When hydroxy groups, mercapto groups, amino groups and/or carboxyl groups of amino acids are protected, they may be protected by a conventional protecting group. For example, the protecting group for hydroxy group is benzyl group, t-butyl group, benzyloxycarbonyl group, etc. The protecting group for mercapto group is benzyl group, benzyloxycarbonyl group, etc. The protecting group for amino group is benzyloxycarbonyl group, t-butoxycarbonyl group, etc. The protecting group for carboxyl group is methyl group, ethyl group, methoxyethyl group, methoxyethoxyethyl group, amino group, etc.

The aryl group for $R^1$ and $R^2$ includes any aromatic hydrocarbon groups such as phenyl group and naphthyl group. The substituent for the aryl group includes a lower alkyl group, a lower alkoxy group or a halogen atom.

The heterocyclic group which is formed by combining $R^1$ and $R^2$ at their termini together with the adjacent nitrogen atom to which they bond may be either a heteromonocyclic group or a heterobicyclic group, and may contain a heteroatom selected from a nitrogen atom, an oxygen atom and a sulfur atom, in addition to the nitrogen atom forming an amide group.

The heterocyclic group includes, for example, a 5- to 6-membered partially saturated or unsaturated aromatic monocyclic group (e.g. pyrrolyl group, pyridyl group, pyrazinyl group, pyrimidinyl group, pyridazinyl group, imidazolyl group, pyrazolyl group, thiazolyl group, tetrazolyl group), a 5- to 6-membered aliphatic monocyclic group (e.g. pyrrolidinyl group, piperidinyl group, piperazinyl group, morpholinyl group, oxazolidinyl group, thiazolidinyl group), a partially saturated or unsaturated aromatic bicyclic group which is formed by condensing a 5- to 6-membered cyclic group and a 5- to 6-membered cyclic group (e.g. quinolyl group, indolyl group, indazolyl group, benzoxazolidinyl group, benzothiazolidinyl group, benzoxazinyl group, benzothiazinyl group), or an aliphatic bicyclic group which is formed by condensing a 5- to 6-membered cyclic group and a 5- to 6-membered cyclic group (e.g. decahydroquinolyl group, octahydro-1H-indolyl group).

The above heterocyclic groups may optionally have a substituent, and the substituent includes an electron-donating group (e.g. amino group, hydroxy group, a lower alkyl group, a lower alkoxy group, a cycloalkyl group) or an electron-withdrawing group (e.g. oxo group, nitro group, a halogen atom, carboxyl group, a lower alkoxycarbonyl group). Preferable heterocyclic group is a heterocyclic group having an electron-withdrawing group.

Suitable examples of the heterocyclic group which is formed by combining $R^1$ and $R^2$ at their termini together with the adjacent nitrogen atom to which they bond are the groups of the following formulae.

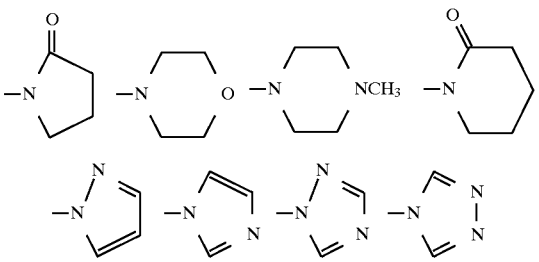

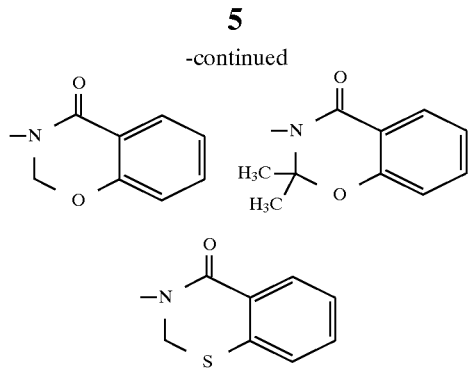

Among the examples of the substituents $R^1$ and $R^2$, preferable combinations of $R^1$ and $R^2$ are (a) each of them is a hydrogen atom, and (b) one of them is a hydrogen atom, and the other is a lower alkyl group.

The combination that each of $R^1$ and $R^2$ is a hydrogen atom is the most preferred.

The substituent on the piperazinyl-lower alkyl group for $R^3$ may be a phenyl group or a phenyl group being substituted by a group selected from a lower alkyl group, a lower alkoxy group, a lower alkylenedioxy group and a halogen atom. The substituted piperazinyl-lower alkyl group for $R^3$ is, for example, 3-[4-(2-methoxyphenyl)piperazinyl]propyl group.

The (di-lower alkylamino)-lower alkyl group for $R^3$ is, for example, 2-(dimethylamino)ethyl group.

The most preferred example of $R^3$ is a hydrogen atom.

Among the propionamide derivatives [I], the preferable ones are the compounds of the formula [I] wherein Ring A is a partial structure of the formula [VI] ($R^4$ is a hydrogen atom, a chlorine atom, a methyl group or a benzyl group), Ring B is a 4-methylphenyl group or 4-methoxyphenyl group, $R^3$ is a hydrogen atom, a 2-dimethylaminoethyl group or a 3-[4-(2-methoxyphenyl)piperazinyl]-propyl group, and each of $R^1$ and $R^2$ is a hydrogen atom or one of $R^1$ and $R^2$ is a hydrogen atom and the other is a methyl group.

Among the propionamide derivatives [I], the more preferable ones are compounds of the formula [I] wherein (i) Ring A is a partial structure of the formula [VI] ($R^4$ is a hydrogen atom or a chlorine atom), Ring B is 4-methoxyphenyl group, $R^3$ is a hydrogen atom or 2-(dimethylamino)ethyl group, (ii) Ring A is a partial structure of the formula [VI] ($R^4$ is a methyl group), Ring B is a 4-methylphenyl group, $R^3$ is a hydrogen atom or 2-(dimethylamino)ethyl group, or (iii) Ring A is a partial structure of the formula [VI] ($R^4$ is a chlorine atom), Ring B is a 4-methoxyphenyl group, $R^3$ is a hydrogen atom or 3-[4-(2-methoxyphenyl)piperazinyl]propyl group, (iv) Ring A is a partial structure of the formula [VI] ($R^4$ is a benzyl group), Ring B is a 4-methoxyphenyl group, $R^3$ is a hydrogen atom or a 2-(dimethylamino)ethyl group, and $R^1$ and $R^2$ are both a hydrogen atom, or one of $R^1$ and $R^2$ is a hydrogen atom and the other is methyl group.

The propionamide derivative [I] may be used in the form of a salt thereof in the cyclization reaction of the present invention. The salt thereof includes, for example, a salt with an inorganic acid or organic acid (e.g. hydrochloride, sulfate, phosphate, hydrobromide, methanesulfonate, p-toluenesulfonate, acetate, fumarate, maleate, oxalate, benzenesulfonate, etc.).

The intramolecular cyclization reaction of the present invention may be carried out in the presence or absence of an acid or a base, but preferably carried out in the presence of an acid.

The acid may be either Brønsted acids or Lewis acids. The Brønsted acid may be either an inorganic acid or an organic acid, for example, a mineral acid (e.g. hydrochloric acid, sulfuric acid, phosphoric acid, hydrofluoric acid, hydrobromic acid, perchloric acid, etc.), a lower alkanoic acid (e.g. formic acid, acetic acid, propionic acid, butyric acid, etc.), a hydroxy-substituted lower alkanoic acid (e.g. citric acid, etc.), a halogeno-lower alkanoic acid (e.g. trifluoroacetic acid, etc.), a lower alkanesulfonic acid (e.g. methanesulfonic acid, etc.), an arylsulfonic acid (e.g. p-toluenesulfonic acid, benzenesulfonic acid, etc.), oxalic acid, etc. The Lewis acid includes titanium tetrachloride, aluminum chloride, boron trifluoride, tin chloride, etc.

Among these acids, a mineral acid, a lower alkanesulfonic acid and an arylsulfonic acid are more preferred, and the most preferable examples are methanesulfonic acid, p-toluenesulfonic acid, benzenesulfonic acid, hydrochloric acid, and hydrobromic acid.

The base may be either inorganic bases or organic bases, for example, inorganic bases (e.g. alkali metal hydrogen carbonates, alkali metal carbonates, alkali metal hydroxides, alkaline earth metal hydroxides, alkali metal hydrides, alkali metal amides, alkali metal alkoxides, alkyl alkali metals, alkali metals, alkaline earth metals, etc.), and organic bases (e.g. 1,8-diazabicyclo[5.4.0]-undeca-7-ene, diisopropylethylamine, triethylamine, pyridine, etc.).

The amount of the acid or base is not critical, but it is usually in the range of 0 to 300 mole %, to the amount of the compound [I].

That is, the present process may preferably be carried out by using a Brønsted acid in an amount of 0 to 100 mole %, preferably in an amount of 0 to 50 mole %, or by using a Lewis acid in an amount of 0 to 300 mole %, preferably in an amount of 50 to 200 mole %, or by using a base in an amount of 0 to 300 mole %, to the amount of the compound [I].

The acids or the bases may be added to the reaction mixture either in one portion or in several portions. However, it may be preferable to add the acids or the bases in several portions so as to shorten the reaction time.

The solvent used in the present invention may be any one which does not affect the reaction, for example, water, alcohols (e.g. methanol, ethanol, propanol, etc.), ketones (e.g. acetone, methyl ethyl ketone, etc.), esters (e.g. ethyl acetate, etc.), aromatic hydrocarbons (e.g. benzene, naphthalene, chlorobenzene, o-dichlorobenzene, m-dichlorobenzene, p-dichlorobenzene, o-, m- or p-trichlorobenzene, toluene, mesitylene, xylene, etc.), halogenated hydrocarbons (e.g. methylene chloride, chloroform, carbon tetrachloride, 1,2-dichloroethane, etc.), aliphatic hydrocarbons (e.g. n-hexane, n-heptane, etc.), alicyclic hydrocarbons (e.g. cyclohexane, etc.), aprotic polar solvents (e.g. N,N-dimethylformamide, dimethyl sulfoxide, etc.), ethers (e.g. dioxane, tetrahydrofuran, etc.), and nitrites (e.g. acetonitrile, etc.), but preferable solvents are solvents having a high boiling point of more than 100° C. such as dioxane, mesitylene, xylene, toluene, chlorobenzene, dichlorobenzene or trichlorobenzene, from a viewpoint of reaction velocity.

These solvents may be used alone, but can be used in the form of a mixture of two or more solvents in a suitable ratio, in a single phase or two phases.

Alcohols, aromatic hydrocarbons, ethers and a mixture thereof are more preferred, and the most preferable examples are chlorobenzene, dichlorobenzene, toluene, xylene, and mesitylene.

The amount of the solvent may be in the range of the amount in which the reactant can be dissolved. However, it is preferable to use a smaller amount of solvent in the above range so as to shorten the reaction time.

The intramolecular cyclization reaction is preferably carried out in a solvent at a temperature between 0° and 250° C., preferably at a temperature between 80° and 200° C.

The propionamide derivative [I] used in the present invention may be either optically active ones or a racemic mixture thereof. When an optically active compound [I] is used in the present invention, the optically active desired compound [II] can be obtained without racemization. The desired compound [II] can optionally be treated with an acid or a base to be converted into an acid addition salt such as hydrochloride, sulfate, phosphate, hydrobromide, methanesulfonate, p-toluenesulfonate, acetate, fumarate, maleate, oxalate, benzenesulfonate, etc., or into an alkali metal salt (e.g. sodium salt, potassium salt, etc.), an alkaline earth metal salt (e.g. magnesium salt, calcium salt, etc.).

The 1,5-benzothiazepine derivative [II] thus obtained or a salt thereof can be converted into a 3-lower alkanoyloxy-5-(di-lower alkylamino-lower alkyl or substituted or unsubstituted piperazinyl-lower alkyl)-2,3-dihydro-2-(substituted phenyl)-1,5-benzothiazepine derivative of the formula:

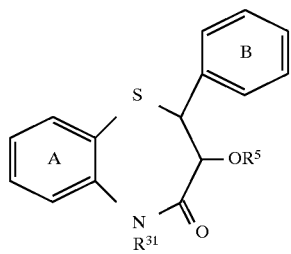

[III]

wherein $R^{31}$ is a (di-lower alkylamino)-lower alkyl group or a piperazinyl-lower alkyl group having optionally a substituent, $R^5$ is a lower alkanoyl group, and Ring A and Ring B are the same as defined above by a method disclosed in Japanese Patent Second Publication (Kokoku) Nos. 43785/1971, 18038/1978, U.S. Pat. Nos. 3,562,257, 4,438,035, 4,567,175, 5,134,139, 5,378,698, etc., the disclosure of which is herein incorporated by reference, and if necessary, further converted into a pharmaceutically acceptable salt thereof.

That is, when $R^3$ of the compound [II] is a hydrogen atom, a (di-lower alkylamino)-lower alkyl group or a substituted or unsubstituted piperazinyl-lower alkyl group is introduced into the 5-position of the 1,5-benzothiazepine derivative [II], and the 3-hydroxy group thereof is acylated with a lower alkanoyl group, and if required, the product thus obtained is converted into a pharmaceutically acceptable salt thereof.

The pharmaceutically acceptable salt may be an acid addition salt with an inorganic acid or an organic acid, for example, hydrochloride, sulfate, phosphate, hydrobromide, methanesulfonate, p-toluenesulfonate, acetate, fumarate, maleate, oxalate and benzenesulfonate.

When the intramolecular cyclization reaction of the present invention is carried out by using the propionamide derivative [I] wherein $R^3$ is a hydrogen atom, and a reagent which may be capable of introducing a (di-lower alkylamino)-lower alkyl group or a piperazinyl-lower alkyl group having optionally a substituent (e.g. (di-lower alkylamino)-lower alkyl halide, or a piperazinyl-lower alkyl halide having optionally a substituent, etc.) is simultaneously added to the reaction system, there can be obtained in a substantially single step a 1,5-benzothiazepine derivative [II] wherein the 5-position of the 1,5-benzothiazepine nucleus is substituted by a di-lower alkylamino-lower alkyl group or a piperazinyl-lower alkyl group having optionally a substituent.

The starting propionamide derivative [I] used in the present invention is a novel compound, and can be prepared, for example, by refluxing a 2-aminothiophenol derivative of the formula [IV]:

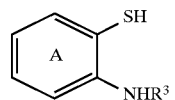

[IV]

wherein Ring A and $R^3$ are the same as defined above, with a 2,3-epoxypropionamide derivative of the formula [V]:

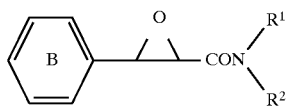

[V]

wherein Ring B, $R^1$ and $R^2$ are the same as defined above, in a suitable solvent in the presence or absence of an iron catalyst.

The solvent may be methanol, benzene, toluene, xylene, mesitylene, chlorobenzene, dichlorobenzene, trichlorobenzene or naphthalene, and methanol, xylene, chlorobenzene and dichlorobenzene are preferred. The iron catalyst may be inorganic or organic salts or complexes having a bivalent or trivalent iron ion, for example, ferric nitrate, iron oxyhydroxide, ferric chloride, ferrous chloride, ferrous sulfate, ferrous iodide, ferrous sulfide, iron 4-cyclohexylbutyrate, ferric oxide, ferric bromide, ferrous fluoride and ferric fluoride, and ferric chloride, ferrous sulfate, and ferric nitrate are preferred examples.

Among the propionamide derivatives [I], the compound of the formula [I] wherein $R^1$ and $R^2$ are the same or different and are each a hydrogen atom, a lower alkyl group, an amino acid residue, or an aryl group having optionally a substituent, or combine each other at their termini together with the adjacent nitrogen atom to which they bond to form a heterocyclic ring having optionally a substituent may be prepared by reacting a propionic acid ester derivative of the formula [VII]:

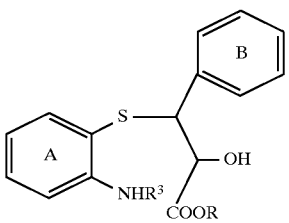

[VII]

wherein R is a lower alkyl group, and Ring A, Ring B and $R^3$ are the same as defined above, with a compound of the formula [VIII-a]:

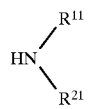

[VIII-a]

wherein $R^{11}$ and $R^{21}$ are the same or different and each are a hydrogen atom, a lower alkyl group, an amino acid residue, or an aryl group having optionally a substituent, or combine each other at their termini together with the adjacent nitrogen atom to which they bond to form a heterocyclic ring having optionally a substituent, in a suitable solvent at a temperature between 0° and 80° C.

The solvent may be methanol, ethanol, tetrahydrofuran, toluene, xylene, mesitylene, chlorobenzene, etc.

If necessary, the amino group of the compound [VII] may be protected by a protecting group such as a benzyloxycarbonyl group, etc., and used in the above reaction, and further said protecting group is removed by a conventional method after the reaction.

Among the 2,3-epoxypropionamide derivatives [V], a (2R,3S)-2,3-epoxypropionamide compound of the formula [V-a]:

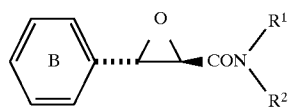

wherein Ring B, $R^1$ and $R^2$ are the same as defined above, and a (2S,3R)-2,3-epoxypropionamide compound of the formula [V-b]:

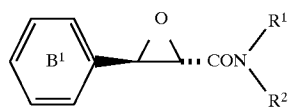

wherein Ring B is a benzene ring being substituted by a lower alkyl group, and $R^1$ and $R^2$ are the same as defined above, are both novel compounds.

The compounds [V-a] and [V-b] wherein each of $R^1$ and $R^2$ is a hydrogen atom or one of $R^1$ and $R^2$ is a hydrogen atom and the other is a lower alkyl group are more preferred, and the most preferable examples are the compounds [V-a] and [V-b] wherein each of $R^1$ and $R^2$ is a hydrogen atom.

Among the 2,3-epoxypropionamide derivatives [V], the compound of the formula [V] wherein $R^1$ and $R^2$ are the same or different and each are a hydrogen atom, a carbamoyl group, a lower alkyl group, an amino acid residue, or an aryl group having optionally a substituent, or combine each other at their termini together with the adjacent nitrogen atom to which they bond to form a heterocyclic group having optionally a substituent may be prepared by reacting a compound of the formula [IX]:

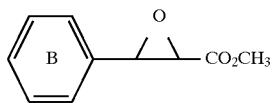

wherein Ring B is the same as defined above, with the compound [VIII-a] in a solvent such as methanol, tetrahydrofuran, dimethylformamide, toluene, xylene, etc., at a temperature between 0° and 100° C.

The compound [V] may be prepared by reacting a reactive derivative (e.g. acid chloride, acid anhydride, etc.) of a compound of the formula [X]:

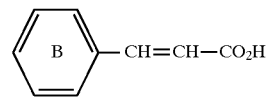

wherein Ring B is the same as defined above, with a compound of the formula [VIII]:

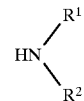

wherein $R^1$ and $R^2$ are the same as defined above, in the presence of a base (e.g. potassium carbonate, sodium hydroxide, sodium hydrogen carbonate, triethylamine, pyridine, etc.), in a solvent such as methylene chloride, tetrahydrofuran, toluene, xylene, etc., at a temperature between 0° and 100° C., and reacting the resulting product of the formula [XI]:

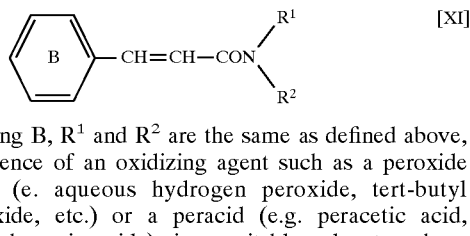

wherein Ring B, $R^1$ and $R^2$ are the same as defined above, in the presence of an oxidizing agent such as a peroxide compound (e. aqueous hydrogen peroxide, tert-butyl hydroperoxide, etc.) or a peracid (e.g. peracetic acid, m-chloroperbenzoic acid ), in a suitable solvent such as methylene chloride, tetrahydrofuran, chlorobenzene, etc. at a temperature between 0° and 100° C.

In the present description and claims, the lower alkyl group means a straight chain or branched chain alkyl group having 1 to 6 carbon atoms, and the lower alkoxy group means a straight chain or branched chain alkoxy group having 1 to 6 carbon atoms. The lower alkylenedioxy group means a straight chain or branched chain alkylenedioxy group having 1 to 6 carbon atoms, and the lower alkanoyl group means a straight chain or branched chain alkanoyl group having 1 to 7 carbon atoms. The cycloalkyl group means a cycloalkyl group having 3 to 8 carbon atoms, and the lower alkanoic acid means a straight chain or branched chain alkanoic acid having 1 to 7 carbon atoms. The halogen atom is chlorine atom, bromine atom, fluorine atom or iodine atom.

The present invention is illustrated in more detail by the following Examples and Reference Examples, but should not be construed to be limited thereto.

EXAMPLES

Example 1

A mixture of (2S,3S)-3-(2-aminophenylthio)-2-hydroxy-3-(4-methoxy-phenyl)propionamide (1.59 g), xylene (8 ml) and methanesulfonic acid (24 mg) is refluxed for 11 hours. After allowed to cool to room temperature, the mixture is stirred to crystallization. The precipitated crystals are collected by filtration, washed with chilled methanol, and dried at 50° C. to give (2S,3S)-2,3-dihydro-3-hydroxy-2-(4-methoxyphenyl)-1,5-benzothiazepin-4(5H)-one (1.41 g).

M.p. 203°–205° C.; $[\alpha]_D^{25}$: +114.3° (c=0.5, dimethylformamide); $^1$H-NMR (DMSO-$d_6$, δ): 3.76 (3H, s), 4.30 (1H, dd), 4.74 (1H, d), 5.05 (1H, d), 6.87–7.62 (8H, m), 10.32 (1H, s); Optical purity (HPLC): >99.9% ee Conditions for HPLC:
Column: CHIRALCEL OD (4.6×250 mm), manufactured by Daicel Chemical Industries, Ltd.
Solvent: n-Hexane: ethanol=85:15
Flow rate: 0.5 ml/min.
UV detective: 254 nm
Column temperature: 35° C.

Example 2

A mixture of (2S,3S)-3-(2-aminophenylthio)-2-hydroxy-3-(4-methoxyphenyl)propionamide (159 mg) and xylene (3 ml) is refluxed for 29 hours. After allowed to cool to room temperature, the mixture is stirred to crystallization. The precipitated crystals are collected by filtration, washed with xylene, and dried at 60° C. to give (2S,3S)-2,3-dihydro-3-hydroxy-2-(4-methoxyphenyl)-1,5-benzothiazepin-4(5H)-one (1 15 mg).

The physical properties of this product are identical to those of the compound of Example 1.

Example 3

A mixture of (2S,3S)-3-(2-aminophenylthio)-2-hydroxy-3-(4-methoxyphenyl)-N-methylpropionamide, chlorobenzene and p-toluenesulfonic acid monohydrate is refluxed. The reaction mixture is subjected to HPLC analysis to confirm the production of (2S,3S)-2,3-dihydro-3-hydroxy-2-(4-methoxyphenyl)-1,5-benzothiazepin-4(5H)-one.

Conditions for HPLC:
- Column: Waters Puresil 5µ C18 120 Å (4.6×150 mm), manufactured by Waters, Inc.
- Solvent: Acetonitrile: 10 mM potassium dihydrogen phosphate (pH 3)=50:50
- Flow rate: 0.5 ml/min.
- UV detective: 254 nm
- Column temperature: 40° C.

Example 4

(2R,3R)-3-(2-Amino-5-methylphenylthio)-2-hydroxy-3-(4-methylphenyl)-propionamide is treated in the same manner as in Example 1 to give (2R,3R)-2,3-dihydro-3-hydroxy-2-(4-methylphenyl)-8-methyl-1,5-benzothiazepin-4(5H)-one.

M.p. 212°–214° C.; $[\alpha]_D^{25}$: −129.2° (c=1.0, dimethylformamide); $^1$H-NMR (DMSO-$d_6$, δ): 2.29 (6H, s), 4.29 (1H, dd), 4.67 (1H, d), 5.03 (1H, d), 7.02–7.42 (7H, m), 10.20 (1H, s)

Example 5

A mixture of (2R,3S)-3-(4-methoxyphenyl)-2,3-epoxypropionamide (966 mg) and xylene (10 ml) is refluxed with heating under nitrogen atmosphere. When the reflux is started, a mixture of 2-aminothiophenol (689 mg) and ferrous sulfate heptahydrate (0.11 mg) in methanol (0.1 ml) is added immediately into the reaction system, and the mixture is reacted at the same temperature for 5 minutes. To the reaction mixture is added methanesulfonic acid (48 mg), and the mixture is refluxed for 13 hours. The mixture is cooled with ice for two hours, and the precipitated crystals are collected by filtration, washed with methanol, and dried at 50° C. to give (2S,3S)-2,3-dihydro-3-hydroxy-2-(4-methoxyphenyl)-1,5-benzothiazepin-4(5H)-one (1.07 g).

The physical properties of this product are identical to those of the compound of Example 1.

Example 6

A mixture of (2S,3S)-3-(2-aminophenylthio)-2-hydroxy-3-(4-methoxyphenyl)propionamide, boron trifluoride-diethyl ether complex and 1,4-dioxane is refluxed. The reaction mixture is subjected to HPLC analysis to confirm the production of (2S,3S)-2,3-dihydro-3-hydroxy-2-(4-methoxyphenyl)-1,5-benzothiazepin-4(5H)-one.

Conditions for HPLC:
- Column: Waters Puresil 5µ C18 120 Å (4.6×150 mm), manufactured by Waters, Inc.
- Solvent: Acetonitrile: 10 mM potassium dihydrogen phosphate (pH 3)=50:50
- Flow rate: 0.5 ml/min.
- UV detective: 254 nm
- Column temperature: 40° C.

Examples 7–31

The compounds [I] as listed in Tables 1–4 are treated in the same manner as in Examples 1–6 or 32–36 to give the corresponding intramolecularly ring-closed compounds [II].

TABLE 1

| Ex. No. | Ring A | Ring B | -R³ | -NR¹R² | Configuration at the 2- and 3- positions |
|---|---|---|---|---|---|
| 7 | (o-phenylene) | (4-OCH₃-phenyl) | -(CH₂)₂N(CH₃)₂ | —NH₂ | (2S, 3S) |
| 8 | (o-phenylene) | (4-OCH₃-phenyl) | -(CH₂)₂N(CH₃)₂ | —NHCH₃ | (2S, 3S) |

TABLE 1-continued

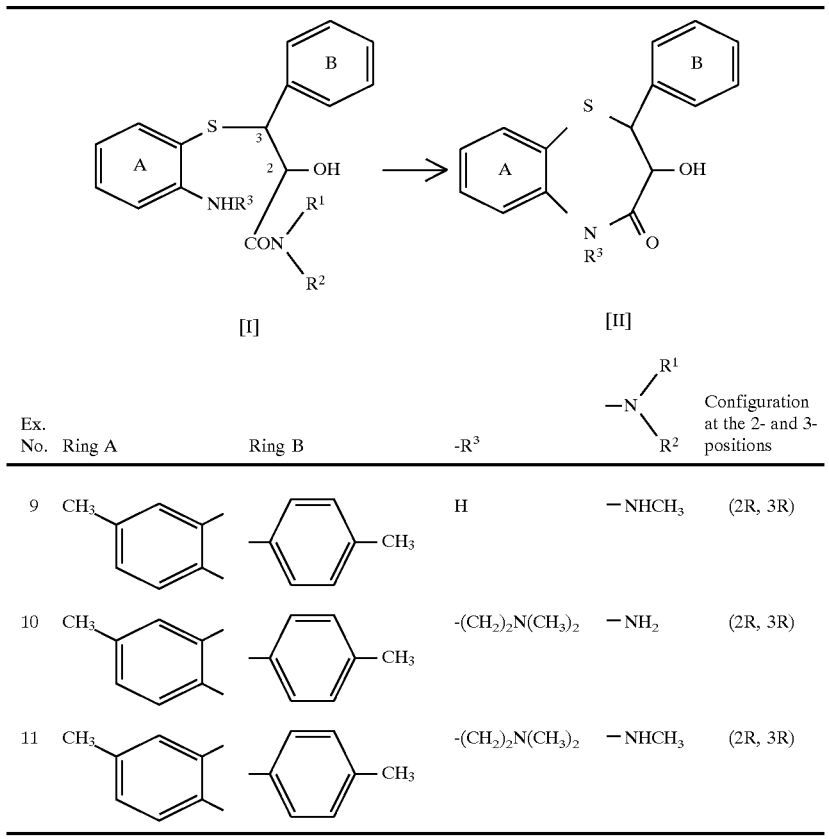

| Ex. No. | Ring A | Ring B | -R³ | -N(R¹)(R²) | Configuration at the 2- and 3- positions |
|---|---|---|---|---|---|
| 9 | CH₃-[benzene]-CH₃ (3,4-dimethyl) | -[benzene]-CH₃ (4-methyl) | H | —NHCH₃ | (2R, 3R) |
| 10 | CH₃-[benzene]-CH₃ (3,4-dimethyl) | -[benzene]-CH₃ (4-methyl) | -(CH₂)₂N(CH₃)₂ | —NH₂ | (2R, 3R) |
| 11 | CH₃-[benzene]-CH₃ (3,4-dimethyl) | -[benzene]-CH₃ (4-methyl) | -(CH₂)₂N(CH₃)₂ | —NHCH₃ | (2R, 3R) |

TABLE 2

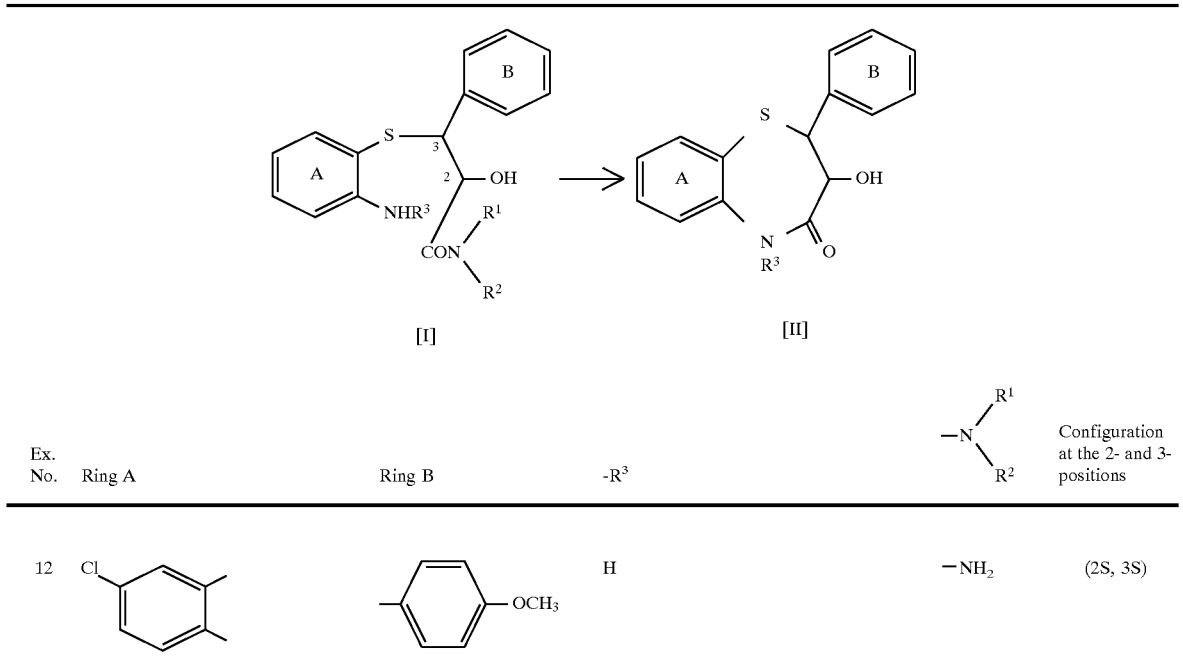

| Ex. No. | Ring A | Ring B | -R³ | -N(R¹)(R²) | Configuration at the 2- and 3- positions |
|---|---|---|---|---|---|
| 12 | Cl-[benzene] (4-chloro) | -[benzene]-OCH₃ (4-methoxy) | H | —NH₂ | (2S, 3S) |

TABLE 2-continued
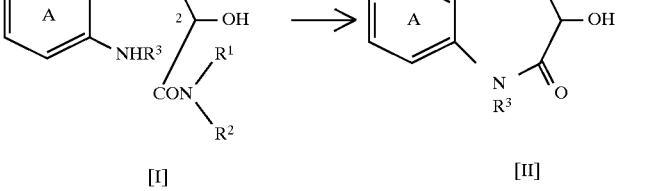
| Ex. No. | Ring A | Ring B | -R³ | —N(R¹)(R²) | Configuration at the 2- and 3- positions |
|---|---|---|---|---|---|
| 13 | 4-Cl-phenyl | 4-OCH₃-phenyl | H | —NHCH₃ | (2S, 3S) |
| 14 | 4-Cl-phenyl | 4-OCH₃-phenyl | —(CH₂)₃—N(piperazinyl)(2-OCH₃-phenyl) | —NH₂ | (2S, 3S) |
| 15 | 4-Cl-phenyl | 4-OCH₃-phenyl | —(CH₂)₃—N(piperazinyl)(2-OCH₃-phenyl) | —NHCH₃ | (2S, 3S) |
| 16 | 4-benzyl-phenyl | 4-OCH₃-phenyl | H | —NH₂ | (2S, 3S) |
| 17 | 4-benzyl-phenyl | 4-OCH₃-phenyl | H | —NHCH₃ | (2S, 3S) |

TABLE 3

[Structure I: 2-aminophenylthio compound with OCH3, OH, CONR1R2 groups] → [Structure II: benzothiazepine ring with OCH3, OH, C=O, NH]

[I] → [II]

| Ex. No. | −N(R¹)(R²) |
|---|---|
| 18 | −NHCONH₂ |
| 19 | −NHCOCH₃ |
| 20 | −N(CH₃)(COCH₃) |
| 21 | −NHCONHCH₃ |
| 22 | −N(CH₃)(CONHCH₃) |
| 23 | −N (2-oxopyrrolidin-1-yl) |
| 24 | −N (morpholino) |
| 25 | −N (4-methylpiperazin-1-yl) |
| 26 | −N (2-oxopiperidin-1-yl) |

TABLE 4

[Structure I] → [Structure II]

| Ex. No. | −N(R¹)(R²) |
|---|---|
| 27 | −N (pyrazol-1-yl) |
| 28 | −N (imidazol-1-yl) |
| 29 | −N (1,2,4-triazol-1-yl) |
| 30 | −N (1,2,3-triazol-1-yl) |
| 31 | −N (3,3-dimethyl-2,3-dihydro-4-oxo-4H-1,3-benzoxazin-3-yl) |

Example 32

(2S,3S)-3-(2-Aminophenylthio)-2-hydroxy-3-(4-methoxyphenyl)-N-phenylpropionamide (582 mg) is mixed with chlorobenzene (10 ml), and the mixture is refluxed for 25 hours during which thereto is added p-toluenesulfonic acid monohydrate (112 mg) in 8 portions (14 mg×8) at intervals of three hours. The reaction mixture is cooled to room temperature, and concentrated under reduced pressure to remove the chlorobenzene. To the residue is added methanol (5 ml), and the mixture is refluxed for one hour. The mixture is allowed to cool to room temperature, and stirred to crystallization, and then cooled with ice. The precipitated crystals are collected by filtration, washed with chilled methanol, and dried at 50° C. to give (2S,3S)-2,3-dihydro-3-hydroxy-2-(4-methoxyphenyl)-1,5-benzothiazepin-4(5H)-one (243 mg).

The physical properties of this product are identical to those of the compound of Example 1.

Example 33

A mixture of (2R,3S)-3-(4-methoxyphenyl)-2,3-epoxypropionamide (3.86 g) and chlorobenzene (77 ml) is refluxed with heating under nitrogen atmosphere. When the reflux is started, a solution of 2-aminothiophenol (2.75 g) and ferric chloride hexahydrate (0.54 mg) in methanol (0.1 ml) is added immediately into the reaction mixture, and the mixture is reacted at the same temperature for 5 minutes. The reaction mixture is subjected to HPLC analysis* to confirm the production of 3-(2-aminophenylthio)-2-hydroxy-3-(4-methoxyphenyl)propionamide (6.09 g) [(2S,3S)/(2S,3R)=91.5/8.5]. To the reaction mixture is added p-toluenesulfonic acid monohydrate (0.76 g), and the mixture is refluxed for 32 hours, and concentrated under reduced pressure to remove the chlorobenzene. To the residue is added methanol (25 ml), and the mixture is refluxed for one hour, and cooled with ice overnight. The precipitated crystals are collected by filtration, washed with methanol, and dried at 50° C. to give (2S,3S)-2,3-dihydro-3-hydroxy-2-(4-methoxyphenyl)-1,5-benzothiazepin-4(5H)-one (4.76 g).

The physical properties of this product are identical to those of the compound of Example 1.

Conditions for HPLC:
  Column: Waters Puresil 5 μm C18 120 Å (4.6×150 mm), manufactured by Waters, Inc.
  Solvent: Acetonitrile: 10 mM potassium dihydrogen phosphate (pH 3)=30:70
  Flow rate: 1.0 ml/min.
  UV detective: 254 nm
  Column temperature: 40° C.

Example 34

A mixture of (2R,3S)-3-(4-methoxyphenyl)-2,3-epoxypropionamide (9.66 g) and chlorobenzene (193 ml) is refluxed with heating under nitrogen atmosphere. When the reflux is started, a solution of 2-aminothiophenol (6.89 g) and ferric chloride hexahydrate (1.35 mg) in methanol (0.1 ml) is added immediately into the reaction mixture, and the mixture is stirred at the same temperature for 5 minutes. The reaction mixture containing (2S,3S)-3-(2-aminophenylthio)-2-hydroxy-3-(4-methoxyphenyl)propionamide is refluxed for 15 hours during which p-toluenesulfonic acid monohydrate (2.88 g) is added thereto in 6 portions (0.48 g×6) at intervals of 2.5 hours to remove the chlorobenzene. The remaining chlorobenzene is evaporated, and methanol (50 ml) is added to the residue. The mixture is refluxed for one hour, allowed to cool to room temperature, and further cooled at 3° C. overnight. The precipitated crystals are collected by filtration, washed with chilled methanol, and dried at 50° C. to give (2S,3S)-2,3-dihydro-3-hydroxy-2-(4-methoxyphenyl)-1,5-benzothiazepin-4(5H)-one (11.73 g).

The physical properties of this product are identical to those of the compound of Example 1.

Example 35

A mixture of (2R,3S)-3-(4-methoxyphenyl)-2,3-epoxypropionamide (1.93 g) and chlorobenzene (39 ml) is refluxed with heating under nitrogen atmosphere. When the reflux is started, a solution of 2-aminothiophenol (1.38 g) and ferric chloride hexahydrate (0.27 mg) in methanol (0.05 ml) is added immediately to the reaction mixture, and the mixture is stirred at the same temperature for 5 minutes to give a reaction mixture containing 3-(2-aminophenylthio)-2-hydroxy-3-(4-methoxyphenyl)propionamide (3.08 g) [(2S,3S)/(2S,3R)=91.3/8.7]. The resulting reaction mixture is concentrated to 16 g. The concentrated mixture is refluxed for 13 hours during which thereto is added methanesulfonic acid (38 mg) in 5 portions (38 mg×5) at intervals of 2–3 hours. The remaining chlorobenzene is evaporated from the mixture, and methanol (10 ml) is added to the residue. The mixture is refluxed for one hour, allowed to cool to room temperature, and further cooled at 8° C. for 40 hours. The precipitated crystals are collected by filtration, washed with chilled methanol, and dried at 50° C. to give (2S,3S)-2,3-dihydro-3-hydroxy-2-(4-methoxyphenyl)-1,5-benzothiazepin-4(5H)-one (2.38 g).

The physical properties of this product are identical to those of the compound of Example 1.

Example 36

A mixture of (2R,3S)-3-(4-methoxyphenyl)-2,3-epoxypropionamide (15.46 g) and chlorobenzene (309 ml) is refluxed with heating under nitrogen atmosphere. When the reflux is started, a solution of 2-aminothiophenol (11.02 g) and ferric chloride hexahydrate (2.16 mg) in methanol (0.1 ml) is added immediately to the reaction mixture, and the mixture is stirred at the same temperature for 5 minutes to give a reaction mixture containing 3-(2-aminophenylthio)-2-hydroxy-3-(4-methoxyphenyl)propionamide (24.24 g) [(2S,3S)/(2S,3R)=91.3/8.7]. A quarter of the mixture is obtained, and 35% hydrochloric acid (1.04 g) is added thereto. The mixture is refluxed for 13 hours to remove the solvent. The remaining chlorobenzene is evaporated from the mixture, and methanol (25 ml) is added to the residue. The mixture is refluxed for one hour, allowed to cool to room temperature, and further cooled at 3° C. overnight. The precipitated crystals are collected by filtration, washed with chilled methanol, and dried at 50° C. to give (2S,3S)-2,3-dihydro-3-hydroxy-2-(4-methoxyphenyl)-1,5-benzothiazepin-4(5H)-one (4.49 g).

The physical properties of this product are identical to those of the compound of Example 1.

Example 37

(2R,3S)-3-(4-Methoxyphenyl)-2,3-epoxypropionamide is treated in the same manner as in Example 36 except for using hydrobromic acid instead of hydrochloric acid to give (2S,3S)-2,3-dihydro-3-hydroxy-2-(4-methoxyphenyl)-1,5-benzothiazepin-4(5H)-one.

The physical properties of this product are identical to those of the compound of Example 1.

Reference Example 1

(1) To a mixture of (2R,3S)-3-(4-methoxyphenyl)-2,3-epoxypropionic acid methyl ester (2.08 g) and N,N-dimethylformamide (3 ml) is added 28% aqueous ammonia (6.1 g) under ice-cooling. The mixture is reacted at room temperature for two hours, and the precipitated crystals are collected by filtration, washed with water, and dried at 50° C. to give (2R,3S)-3-(4-methoxyphenyl)-2,3-epoxypropionamide (1.64 g).

M.p. 142°–144° C.; $[\alpha]_D^{25}$: −163.7° (c=1.0,methanol); $^1$H-NMR (DMSO-d$_6$, δ): 3.49 (1H, d), 3.75 (3H, s), 3.96 (1H, d), 6.94 (2H, d), 7.24 (2H, d), 7.41 (1H, s), 7.56 (1H, s)

(2) A mixture of (2R,3S)-3-(4-methoxyphenyl)-2,3-epoxypropionamide (1.93 g) and xylene (15 ml) is refluxed with heating under nitrogen atmosphere. When the reflux is started, a solution of 2-aminothiophenol (1.38 g) and ferrous sulfate heptahydrate (0.28 mg) in methanol (0.2 ml) is added immediately into the reaction mixture, and the mixture is reacted at the same temperature for 5 minutes, and cooled to room temperature. The reaction mixture is subjected to HPLC analysis to confirm the production of 3-(2-aminophenylthio)-2-hydroxy-3-(4-methoxyphenyl)propionamide (2.69 g, (2S,3S)/-(2S,3R)=91/9). The reaction mixture is concentrated under reduced pressure to remove the solvent, and the residue is dissolved with heating in ethanol (3 ml) and water (3 ml). The mixture is gradually cooled to 0° C. with stirring to crystallization. The precipitated crystals are collected by filtration, washed with chilled 50% ethanol, and dried at 50° C. to give (2S,3S)-3-(2-aminophenylthio)-2-hydroxy-3-(4-methoxyphenyl)propionamide (0.84 g).

M.p. 110°–112° C.; $[\alpha]_D^{25}$: +506° (c=1.0, methanol); $^1$H-NMR (DMSO-d$_6$, δ): 3.70 (3H, s), 4.11 (1H, dd), 4.44 (1H, d), 5.35 (2H, s), 6.02 (1H, d), 6.25–7.28 (8H, m), 7.39 (2H, s)

Conditions for HPLC:
  Column: Waters Puresil 5μ C18 120 Å (4.6×150 mm), manufactured by Waters, Inc.
  Solvent: Acetonitrile: 10 mM potassium dihydrogen phosphate (pH 3)=30:70
  Flow rate: 1.0 ml/min.
  UV detective: 254 nm
  Column temperature: 40° C.

Reference Example 2

(1) (2R,3S)-3-(4-Methoxyphenyl)-2,3-epoxypropionic acid methyl eater (2.08 g) is mixed with methanol (10 ml), and thereto is added dropwise a solution of 40% aqueous methylamine (1.44 g) in methanol (10 ml) under ice-cooling. The reaction mixture is stirred at 10°–15° C. for two hours, and concentrated under reduced pressure to remove the methanol. To the residue is added ether, and the precipitated crystals are collected by filtration, washed, and dried under reduced pressure at 50° C. to give (2R,3S)-3-(4-methoxyphenyl)-2,3-epoxy-N-methylpropionamide (1.70 g).

M.p. 135°–136° C.; $[\alpha]_D^{25}$: −145.3° (c=1.0, methanol); $^1$H-NMR (CDCl$_3$, δ): 2.86 (3H, d), 3.53 (1H, d), 3.81 (3H, s), 3.83 (1H, d), 6.26 (1H, s), 6.84–7.26 (4H, m)

(2) A mixture of (2R,3S)-3-(4-methoxyphenyl)-2,3-epoxy-N-methylpropionamide (829 mg) and xylene (10 ml) is refluxed with heating under nitrogen atmosphere. When the reflux is started, a solution of 2-aminothiophenol (551 mg) and anhydrous ferric chloride (0.065 mg) in methanol (0.08 ml) is added immediately into the reaction mixture, and the mixture is reacted at the same temperature for 5 minutes, and cooled to room temperature. The precipitated crystals are collected by filtration, washed with xylene, and dried at 60° C. to give (2S,3S)-3-(2-aminophenylthio)-2-hydroxy-3-(4-methoxyphenyl)-N-methylpropionamide (1.06 g).

M.p. 145°–147° C.; $[\alpha]_D^{25}$: +433° (c=1.0, methanol); $^1$H-NMR (DMSO-d$_6$, δ): 2.63 (3H, d), 3.70 (3H, s), 4.14 (1H, dd), 4.45 (1H, d), 5.33 (2H, s), 6.11 (1H, d), 6.25–7.29 (8H, m), 7.93 (1H, d)

Reference Example 3

(1) To a mixture of (2S,3R)-3-(4-methylphenyl)-2,3-epoxypropionic acid methyl ester (3.84 g) and methanol (25 ml) is added dropwise a solution of 28% aqueous ammonia (6.1 g) in methanol (10 ml) under ice-cooling. The reaction mixture is gradually warmed to room temperature, and stirred for two hours, and further stirred for one hour under ice-cooling. The precipitated crystals are collected by filtration, washed, and dried at 50° C. to give (2S,3R)-3-(4-methylphenyl)-2,3-epoxypropionamide (2.71 g).

M.p. 183°–185° C.; $[\alpha]_D^{25}$: +172.5° (c=1, methanol); $^1$H-NMR (CDCl$_3$ and DMSO-d$_6$, δ): 2.35 (3H, s), 3.47 (1H, d), 3.93 (1H, d), 6.52 (2H, d), 7.16 (4H, s)

(2) (2S,3R)-3-(4-Methylphenyl)-2,3-epoxypropionamide and 2-amino-5-methylthiophenol are treated in the same manner as in Reference Example 1-(2) to give (2R,3R)-3-(2-amino-5-methylphenylthio)-2-hydroxy-3-(4-methylphenyl)propionamide.

M.p. 145°–146° C.; $[\alpha]_D^{25}$: −410° (c=1, methanol); $^1$H-NMR (DMSO-d$_6$, δ): 1.96 (3H, s), 2.24 (3H, s), 4.11 (1H, dd), 4.46 (1H, d), 5.13 (2H, s), 5.99 (1H, d), 6.51–7.26 (7H, m), 7.37 (2H, s)

Reference Example 4

(1) To a mixture of (2S,3R)-3-(4-methylphenyl)-2,3-epoxypropionic acid methyl ester (1.92 g) and methanol (10 ml) is added dropwise a solution of 40% aqueous methylamine solution (2.37 g) in methanol (10 ml) under ice-cooling. The reaction mixture is stirred under ice-cooling for one hour, and concentrated under reduced pressure. To the residue is added ether, and the precipitated crystals are collected by filtration, washed, and dried at 50° C. to give (2S,3R)-3-(4-methylphenyl)-2,3-epoxy-N-methylpropionamide (1.75 g).

M.p. 152°–153° C.; $[\alpha]_D^{25}$: +153.7° (c=1, methanol); $^1$H-NMR (CDCl$_3$, δ): 2.34 (3H, s), 2.86 (3H, d), 3.52 (1H, d), 3.83 (2H, d), 6.27 (1H, s), 7.15 (4H, s)

(2) (2S,3R)-3-(4-Methylphenyl)-2,3-epoxy-N-methylpropionamide and 2-amino-5-methylthiophenol are treated in the same manner as in Reference Example 1-(2) to give (2R,3R)-3-(2-amino-5-methylphenylthio)-2-hydroxy-3-(4-methylphenyl)-N-methylpropionamide.

M.p. 168°–170° C.; $[\alpha]_D^{25}$: −379° (c=1, methanol); $^1$H-NMR (DMSO-d$_6$, δ): 1.97 (3H, s), 2.25 (3H, s), 2.62

(3H, d), 4.13 (1H, dd), 4.47 (1H, d), 5.12(2H, s), 6.10 (1H, d), 6.51–7.27(7H, m), 7.94(1H, d)

Reference Example 5

To a mixture of (2S,3S)-3-(2-aminophenylthio)-2-hydroxy-(4-methoxy-phenyl)propionic acid methyl ester and methanol is added dropwise aqueous ammonia under ice-cooling. The reaction mixture is reacted at room temperature, and the precipitated crystals are collected by filtration, washed with water, and dried to give (2S,3S)-3-(2-aminophenylthio)-2-hydroxy-3-(4-methoxyphenyl) propionamide.

Reference Example 6

Potassium carbonate is added to dimethyl sulfoxide, and the mixture is stirred at 70° C. The mixture is cooled to room temperature, and thereto is added (2S,3S)-3-(2-aminophenylthio)-2-hydroxy-3-(4-methoxyphenyl) propionamide, and stirred. To the reaction mixture is added dropwise 2-dimethylaminoethyl chloride, and the mixture is stirred at room temperature. The reaction mixture is poured into ice-water, and extracted with ethyl acetate. The extract is dried, and concentrated under reduced pressure to remove the solvent to give (2S,3S)-3-[2-(2-dimethylaminoethylamino)phenylthio]-2-hydroxy-3-(4-methoxyphenyl)-propionamide.

Reference Example 7

A mixture of (2R,3S)-3-(4-methoxyphenyl)-2,3-epoxypropionamide and xylene is refluxed with heating under nitrogen atmosphere. When the reflux is started, a solution of 2-(2-dimethylaminoethylamino)thiophenol and ferrous sulfate heptahydrate in methanol is added immediately into the reaction mixture, and the mixture is reacted at the same temperature, and cooled to room temperature. The reaction mixture is concentrated under reduced pressure, and the residue is dissolved with heating in ethanol and water. The mixture is allowed to cool to 0° C., and the precipitated crystals are collected by filtration, washed with chilled 50% ethanol, and dried to give (2S,3S)-3-[2-(2-dimethylaminoethylamino)phenylthio]-2-hydroxy-3-(4-methoxyphenyl)propionamide.

Reference Examples 8–30

The corresponding starting compounds are treated in the same manner as in Reference Examples 1–7 or 31–33 to give the compounds as listed in Tables 5–8.

TABLE 5

| Ex. No. | Ring A | Ring B | -R³ | —N(R¹)(R²) | Configuration at the 2- and 3- positions |
|---|---|---|---|---|---|
| 8 | phenyl | 4-OCH₃-phenyl | -(CH₂)₂N(CH₃)₂ | —NHCH₃ | (2S, 3S) |
| 9 | 3-CH₃-phenyl | 4-CH₃-phenyl | -(CH₂)₂N(CH₃)₂ | —NH₂ | (2R, 3R) |
| 10 | 3-CH₃-phenyl | 4-CH₃-phenyl | -(CH₂)₂N(CH₃)₂ | —NHCH₃ | (2R, 3R) |

TABLE 6
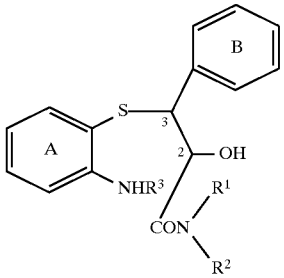
| Ex. No. | Ring A | Ring B | —R³ | —N(R¹)(R²) | Configuration at the 2- and 3- positions |
|---|---|---|---|---|---|
| 11 | 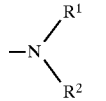 | 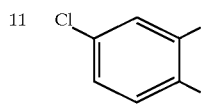 | H | —NH₂ | (2S, 3S) |
| 12 | 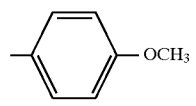 |  | H | —NHCH₃ | (2S, 3S) |
| 13 | 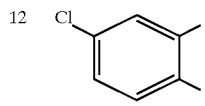 | 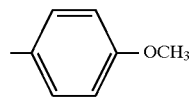 | —(CH₂)₃— | —NH₂ | (2S, 3S) |
| 14 | 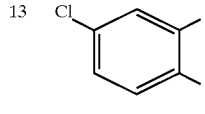 | 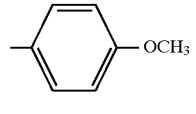 | —(CH₂)₃—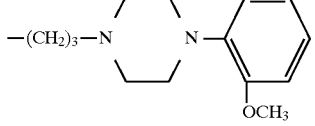 | —NHCH₃ | (2S, 3S) |
| 15 |  | 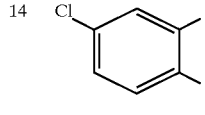 | H | —NH₂ | (2S, 3S) |
| 16 | 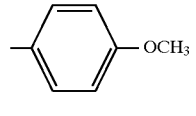 | 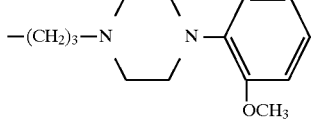 | H | —NHCH₃ | (2S, 3S) |

TABLE 7

Structure: 2-aminophenyl-S-CH(4-methoxyphenyl)-CH(OH)-CON(R¹)(R²)

| Ex. No. | –NR¹R² |
|---|---|
| 17 | –NHCONH₂ |
| 18 | –NHCOCH₃ |
| 19 | –N(CH₃)(COCH₃) |
| 20 | –NHCONHCH₃ |
| 21 | –N(CH₃)(CONHCH₃) |
| 22 | 2-oxopyrrolidin-1-yl |
| 23 | morpholin-4-yl |
| 24 | 4-methylpiperazin-1-yl |
| 25 | 2-oxopiperidin-1-yl |

TABLE 8

Structure: 2-aminophenyl-S-CH(4-methoxyphenyl)-CH(OH)-CON(R¹)(R²)

| Ex. No. | –NR¹R² |
|---|---|
| 26 | pyrazol-1-yl |
| 27 | imidazol-1-yl |
| 28 | 1,2,4-triazol-1-yl |
| 29 | 1,2,3-triazol-1-yl |
| 30 | –N(C(CH₃)₃)–CO–(2-hydroxyphenyl) (lactam form) |

Reference Example 31

(1) To a mixture of sodium hydride (62.5% oil dispersion, 0.46 g) and dimethyl sulfoxide (3 ml) is added a solution of aniline (1.02 g) in dimethyl sulfoxide (1 ml) at room temperature under nitrogen atmosphere, and the mixture is stirred for 30 minutes. To the mixture is added a solution of (2R,3S)-3-(4-methoxyphenyl)-2,3-epoxypropionic acid methyl ester (2.08 g) in dimethyl sulfoxide (4 ml) at room temperature over a period of 15 minutes. The mixture is further stirred at the same temperature for one hour, and thereto is added water (50 ml). The precipitated yellow crystals are collected by filtration, and recrystallized from ethyl acetate (60 ml) to give (2R,3S)-3-(4-methoxyphenyl)-2,3-epoxy-N-phenylpropionamide (1.50 g).

M.p. 162°–163° C.; $[\alpha]_D^{25}$: –223.7° (c=1.0, dimethylformamide); ¹H-NMR (DMSO-d₆, δ): 3.77 (3H, s), 3.78 (1H, d), 4.13 (1H, d), 6.95–7.69 (9H, m), 10.25 (1H, s)

(2) A mixture of (2R,3S)-3-(4-methoxyphenyl)-2,3-epoxy-N-phenylpropionamide (539 mg) and chlorobenzene (5 ml) is refluxed with heating under nitrogen atmosphere. When the reflux is started, a solution of 2-aminothiophenol (275 mg) and ferric chloride hexahydrate (0.054 mg) in methanol (0.1 ml) is added immediately to the reaction mixture. The mixture is stirred at the same temperature for 5 minutes, and cooled to room temperature. The precipitated crystals are collected by filtration, washed with chlorobenzene, and dried at 50° C. to give (2S,3S)-3-(2-aminophenylthio)-2-hydroxy-3-(4-methoxyphenyl)-N-phenylpropionamide (582 mg).

M.p. 215°–217° C.; $[\alpha]_D^{20}$: +437° (c=1.0, dimethylformamide); $^1$H-NMR (DMSO-$d_6$, δ): 3.69 (3H, s), 4.35 (1H, d), 4.51 (1H, d), 5.31 (2H, s), 6.24–7.69 (13H, m), 6.52 (1H, s), 9.83 (1H, s)

Reference Example 32

(2R,3S)-3-(4-Methoxyphenyl)-2,3-epoxypropionic acid methyl ester (10.4 g) is mixed with 15.3 wt % solution of ammonia in methanol (56 g), and the mixture is reacted at 15° C. for 2.5 hours. The mixture is concentrated under reduced pressure until the total weight of the mixture becomes 44 g. To the mixture is added ice-water (112 g), and the mixture is stirred for two hours under ice-cooling. The precipitated crystals are collected by filtration, washed with water, and dried at 50° C. to give (2R,3S)-3-(4-methoxyphenyl)-2,3-epoxypropionamide (8.99 g).

Reference Example 33

(2S,3S)-3-(2-Aminophenylthio)-2-hydroxy-3-(4-methoxyphenyl)-propionic acid methyl ester and aniline are treated in the same manner as in Reference Example 5 to give (2S,3S)-3-(2-aminophenylthio)-2-hydroxy-3-(4-methoxyphenyl)-N-phenylpropionamide.

EFFECTS OF INVENTION

According to the present invention, the 1,5-benzothiazepine derivative [II], which is an intermediate for preparing medicaments such as diltiazem hydrochloride can be obtained in high yield by intramolecular cyclization reaction of the propionamide derivative [I] having an unprotected 2-hydroxy group. Especially, when the substituents on the amide moiety of the propionamide derivative [I] (i.e. $R^1$ and $R^2$) are both a hydrogen atom, ammonia which is generated during the intramolecular cyclization reaction can be removed in the form of gas from the reaction system, and hence, the intramolecular cyclization reaction of the compound [I] can be easily carried out by simply heating the reaction mixture, without using an acid or a base.

Besides, after the 2-aminothiophenol derivative [IV] and the 2,3-epoxypropionamide derivative [V] are reacted, the resulting propionamide derivative [I] can be used in the present intramolecular cyclization reaction without isolating it from the reaction system. In this case, the desired compound [II] can be obtained from the 2,3-epoxypropionamide derivative [V] in high yield in a single step without complicated procedures.

What is claimed is:

1. A process for preparing a 1,5-benzothiazepine derivative of the formula [II]:

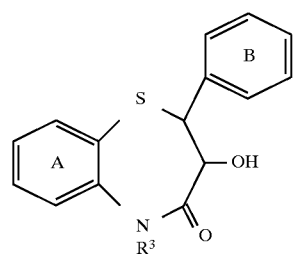

wherein Ring A and Ring B are a substituted or unsubstituted benzene ring, and $R^3$ is a hydrogen atom, a (di-lower alkylamino)-lower alkyl group or a substituted or unsubstituted piperazinyl-lower alkyl group, or a salt thereof, which comprises subjecting a propionamide derivative of the formula [I]:

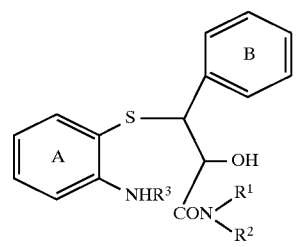

wherein $R^1$ and $R^2$ are the same or different and each are a hydrogen atom, a carbamoyl group, a lower alkyl group, a lower alkanoyl group, a lower alkylaminocarbonyl group, an amino acid residue, or an aryl group having optionally a substituent, or combine with each other at their termini together with the adjacent nitrogen atom to which they bond to form a heterocyclic group having optionally a substituent, and Ring A, Ring B and $R^3$ are the same as defined above, to intramolecular cyclization reaction, and if necessary, converting the product into a salt thereof.

2. A process for preparing a 3-lower alkanoyloxy-5-[di-lower alkylamino-lower alkyl or a substituted or unsubstituted piperazinyl-lower alkyl]-1,5-benzothiazepine derivative of the formula [III]:

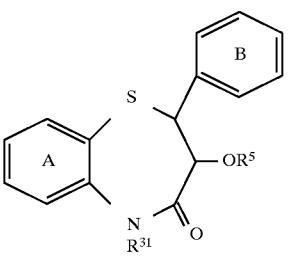

wherein Ring A and Ring B are a substituted or unsubstituted benzene ring, $R^{31}$ is a (di-lower alkylamino)-lower alkyl group or a substituted or unsubstituted piperazinyl-lower alkyl group, and $R^5$ is a lower alkanoyl group, or a pharmaceutically acceptable salt thereof, which comprises subjecting a propionamide derivative of the formula [I]:

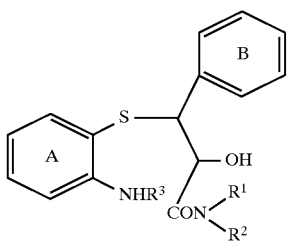

wherein $R^1$ and $R^2$ are the same or different and each are a hydrogen atom, a carbamoyl group, a lower alkyl group, a lower alkanoyl group, a lower alkylaminocarbonyl group, an amino acid residue, or an aryl group having optionally a substituent, or combine with each other at their termini together with the adjacent nitrogen atom to which they bond to form a heterocyclic group having optionally a substituent, $R^3$ is a hydrogen atom, a (di-lower alkylamino)-lower alkyl group or a substituted or unsubstituted piperazinyl-lower alkyl group, and Ring A and Ring B are the same as defined above, or a salt thereof, to intra-molecular cyclization reaction to give a 1,5-benzothiazepine derivative of the formula [II]:

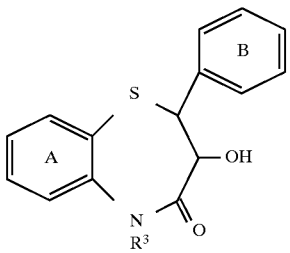

wherein Ring A, Ring B and $R^3$ are the same as defined above, and when $R^3$ of the compound [II] is a hydrogen atom, introducing a (di-lower alkylamino)-lower alkyl group or a substituted or unsubstituted piperazinyl-lower alkyl group into the 5-position of the compound [II], acylating the 3-hydroxy group of the resulting compound with a lower alkanoyl group, and if necessary, converting the product into a pharmaceutically acceptable salt thereof.

3. A process according to claim 1 wherein $R^3$ is a hydrogen atom.

4. A process according to claim 1 wherein each of $R^1$ and $R^2$ is a hydrogen atom or one of $R^1$ and $R^2$ is a hydrogen atom and the other is a lower alkyl group.

5. A process according to claim 4, wherein each of $R^1$ and $R^2$ is a hydrogen atom.

6. A process according to claim 1, wherein each of $R^1$ and $R^2$ is a hydrogen atom or one of $R^1$ and $R^2$ is a hydrogen atom and the other is a lower alkyl group, and $R^3$ is a hydrogen atom.

7. A process according to claim 6, wherein each of $R^1$, $R^2$ and $R^3$ is a hydrogen atom.

8. A process according to claim 1 wherein Ring A is a benzene ring of the formula:

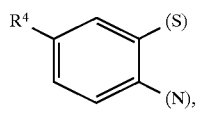

$R^4$ is a hydrogen atom, a halogen atom, a lower alkyl group or a phenyl-lower alkyl group, and Ring B is a 4-lower alkylphenyl group or a 4-lower alkoxyphenyl group.

9. A process according to claim 8 wherein $R^4$ is a hydrogen atom, a halogen atom or a phenyl-lower alkyl group, and Ring B is a 4-lower alkoxyphenyl group.

10. A process according to claim 8 wherein $R^4$ is a lower alkyl group, and Ring B is a 4-lower alkylphenyl group.

11. A process according to claim 1, wherein Ring A is a benzene ring of the formula:

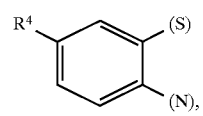

$R^4$ is a hydrogen atom, a chlorine atom, a methyl group or a benzyl group, Ring B is a 4-methylphenyl group or a 4-methoxyphenyl group, each of $R^1$ and $R^2$ is a hydrogen atom or one of $R^1$ and $R^2$ is a hydrogen atom and the other is a methyl group, and $R^3$ is a hydrogen atom, a 2-(dimethylamino)ethyl group or a 3-[4-(2-methoxyphenyl) piperazinyl]propyl group.

12. A process according to claim 11, wherein $R^4$ is a hydrogen atom or a chlorine atom, Ring B is a 4-methoxyphenyl group, and $R^3$ is a hydrogen atom or a 2-(dimethylamino)ethyl group.

13. A process according to claim 11, wherein $R^4$ is a methyl group, Ring B is a 4-methylphenyl group, and $R^3$ is a hydrogen atom or a 2-(dimethylamino)ethyl group.

14. A process according to claim 11, wherein $R^4$ is a chlorine atom, Ring B is a 4-methoxyphenyl group, and $R^3$ is a hydrogen atom or a 3-[4-(2-methoxyphenyl)piperazinyl] propyl group.

15. A process according to claim 11, wherein $R^4$ is a benzyl group, Ring B is a 4-methoxyphenyl group, and $R^3$ is a hydrogen atom or a 2-(dimethylamino)ethyl group.

16. A process according to any one of claims 11, 12, 13, 14 and 15, wherein $R^3$ is a hydrogen atom.

17. A process according to claim 16, wherein each of $R^1$ and $R^2$ is a hydrogen atom.

18. A process according to clam 1, wherein the intramolecular cyclization reaction is carried out in an alcohol, an aromatic hydrocarbon, an ether or a mixture thereof.

19. A process according to claim 18, wherein the intramolecular cyclization reaction is carried out in chlorobenzene, dichlorobenzene, toluene, xylene and mesitylene.

20. A process according to claim 1, wherein the intramolecular cyclization reaction is carried out in the presence of an acid.

21. A process according to claim 20 wherein the intramolecular cyclization reaction is carried out in the presence of a mineral acid, a lower alkanesulfonic acid or an arylsulfonic acid.

22. A process according to claim 21 wherein the intramolecular cyclization reaction is carried out in the presence of methanesulfonic acid, p-toluenesulfonic acid, benzenesulfonic acid, hydrochloric acid, or hydrobromic acid.

* * * * *